US00PP19277P3

(12) United States Plant Patent
Hambuchen et al.

(10) Patent No.: US PP19,277 P3
(45) Date of Patent: Sep. 30, 2008

(54) CREPEMYRTLE TREE NAMED 'CASCADING PINK LADY'

(50) Latin Name: *Lagerstroemia indicia' prostrata'*
Varietal Denomination: Cascading Pink Lady

(76) Inventors: Robert E. Hambuchen, 3040 Dallas Loop, Conway, AR (US) 72034; Betty J. Hambuchen, 3040 Dallas Loop, Conway, AR (US) 72034

( * ) Notice: Subject to any disclaimer, the term of this patent is extended or adjusted under 35 U.S.C. 154(b) by 39 days.

(21) Appl. No.: 11/645,310

(22) Filed: Dec. 26, 2006

(65) Prior Publication Data

US 2008/0155724 P1 Jun. 26, 2008

(51) Int. Cl.
*A01H 5/00* (2006.01)

(52) U.S. Cl. ..... Plt./252
(58) Field of Classification Search ..... Plt./252
See application file for complete search history.

(56) References Cited

U.S. PATENT DOCUMENTS

PP13,965 P3 * 7/2003 Hambuchen et al. ..... Plt./252

* cited by examiner

*Primary Examiner*—Wendy C. Haas

(57) ABSTRACT

'Cascading Pink Lady' is a new distinct variety of *Lagerstroemia indica 'prostrata'*,commonly referred to as Crepemyrtle. It is a low growing variety where the primary limbs cascade out and downward while producing multiple secondary along the primaries. It reaches a height of 16 to 20 inches at maturity with substantially no upward growth. It can reach a width of 36 to 40 inches. This cultivar blooms in mid June in Zone 7B and normally is in full bloom by the end of June. Because of its bloom habit it sometimes appears to be a multi-colored Crepemyrtle. While most new blooms are a Red Purple 72D a few blooms are very lite in color, with some appearing almost white. The plant very resistant to powdery mildew and is cold hardy with no visible damage at 8 degrees Farenheit.

3 Drawing Sheets

Latin name of the genus and species of the plant claimed: *Lagerstroemia indica 'prostrata'*.
Variety denomination: 'Cascading Pink Lady'.

BACKGROUND OF THE INVENTION

1. Field of the Invention

The present invention relates to a new and a very distinct variety of landscape plant, *Lagerstroemia indica* 'Cascading Pink Lady', commonly known as Crepemyrtle.

2. Description of Prior Art Including Information Disclosed Uinder 37 CRF 1,97 and 1.99.

This new and aforementioned cultivar, 'Cascading Pink Lady' is a whole plant sport of 'Rosey Carpet' U.S. Plant Pat. No. 13,965. It was found growing in our cutting bed facility. This new cultivar is a low growing and spreading plant with a cascading growth pattern. This new plant has been propagated from both hardwood and soft wood cuttings over several generations. Each generation of cuttings produce plants identical to the original seedling plant.

SUMMARY OF INVENTION

The invention involves the discovery of a new and distinct variety of Crepemyrtle, *Lagerstroemia indica 'prostrata'* which we have named 'Cascading Pink Lady'. It is characterized as a vigorous, low growing and spreading cultivar with arching or cascading limbs. The plant reaches a height of 16 to 20 inches at maturity with substantially no vertical growth, after maturity providing only cascading limbs. Shortly after the primary limbs develop and grow we start to see secondary limbs develop. During bloom season each secondary produces an inflorescence. This provides color over the entire plant. The stamens on all blooms retain their yellow color well into the life of the bloom but fade and dry up before the bloom falls. In a normal year 'Cascading Pink Lady' starts to bloom in mid June and is in full bloom by the end of June in Central Arkansas, zone 7B. Plants continue to bloom well into October. The Cultivar produces seed but not in heavy or excessive amounts.

DETAILED BOTANICAL DESCRIPTION OF THE PLANT

Figure 1:
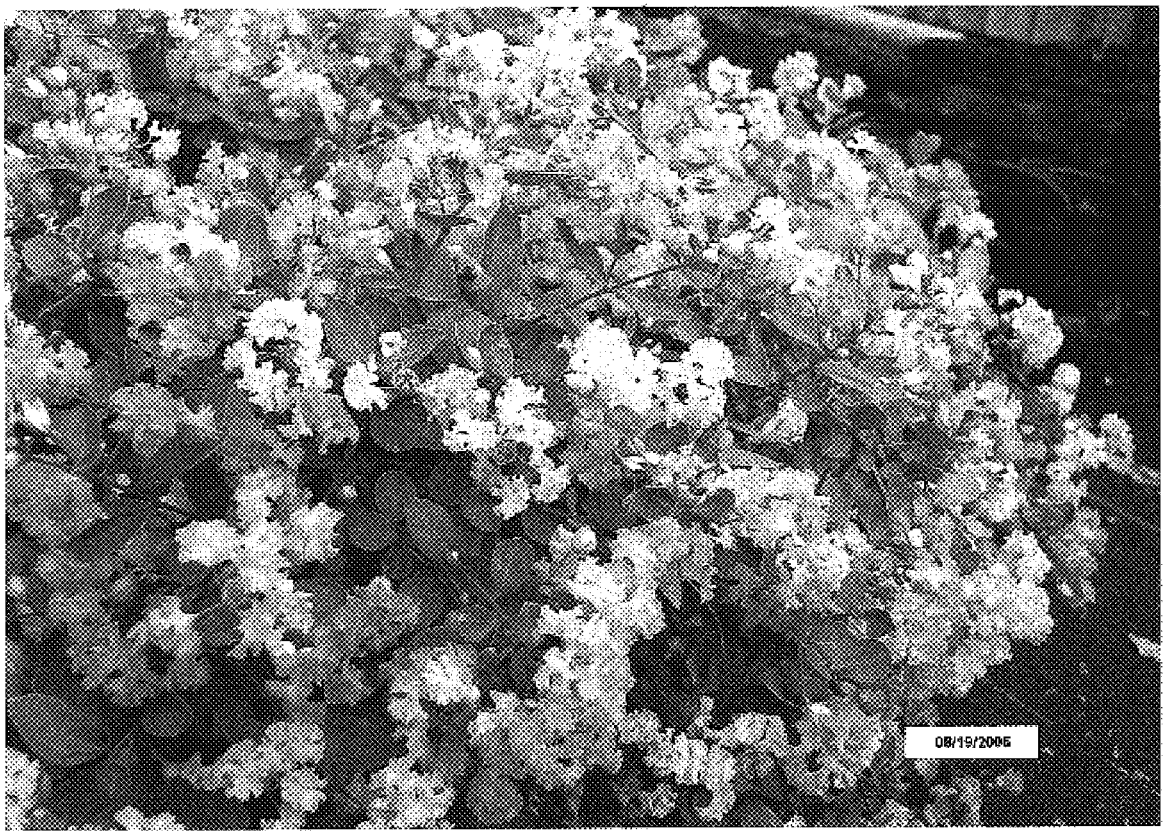
FIG. 1 Close up and partial photo of 'Cascading Pink Lady' in full bloom showing the color variation as the blooms start to mature.
Figure 2:
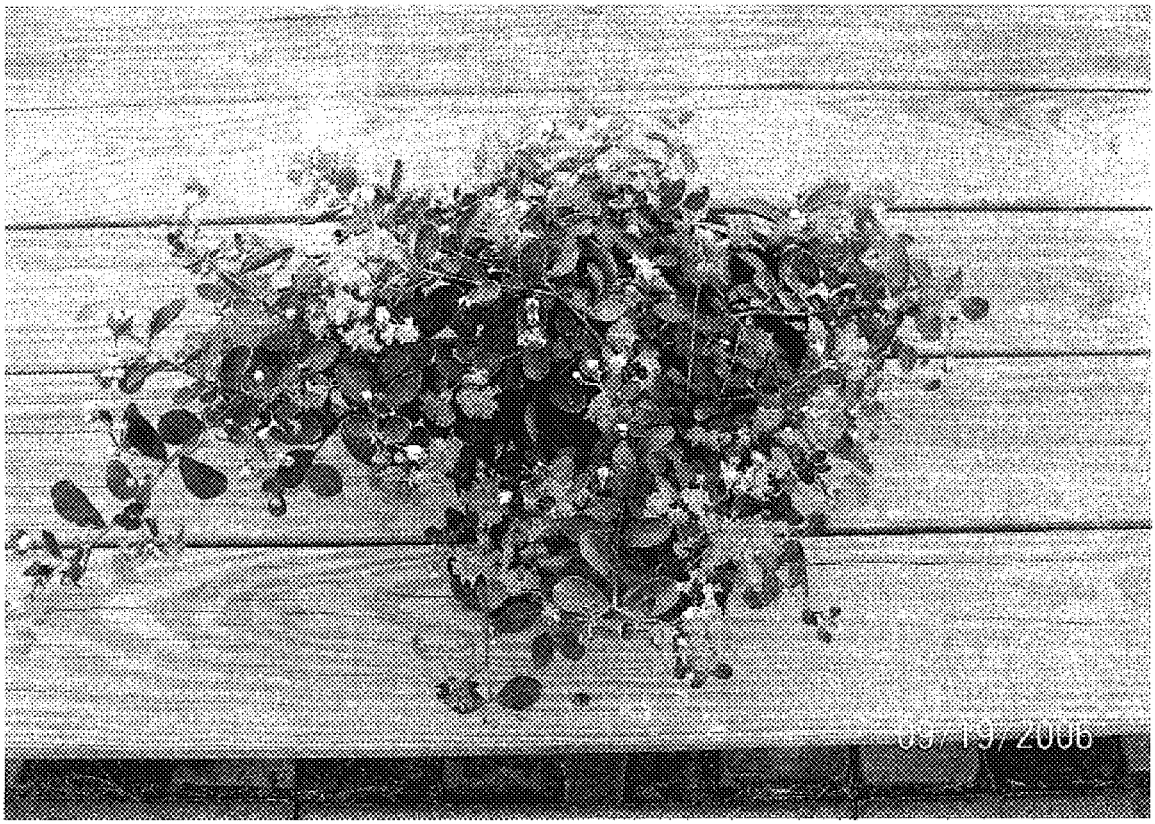
FIG. 2 Recently propagated 3$^{rd}$ generation 'Cascading Pink Lady'.
Figure 3:
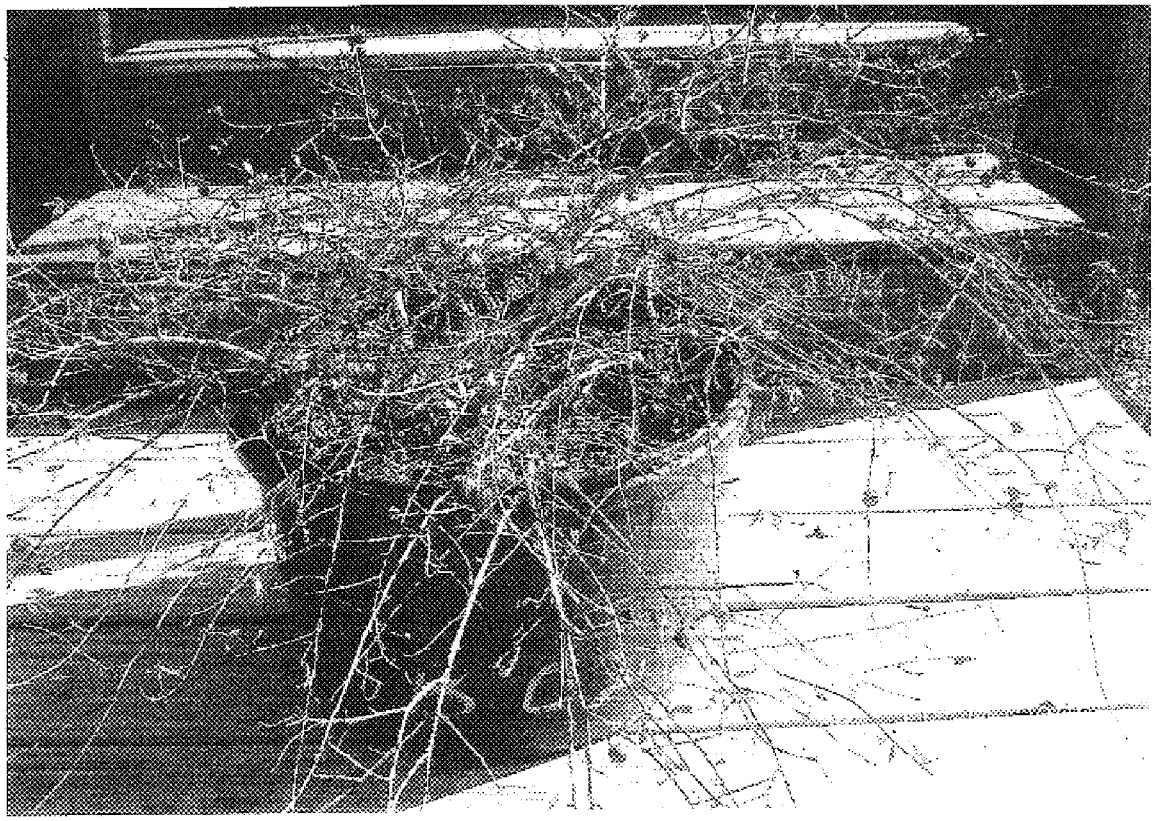
FIG. 3 Picture of the defoliated plant more clearly showing its natural structure.

This new variety of Crepemyrtle, *Lagerstroemia indica* 'prostrata', named 'Cascading Pink Lady' is a whole plant sport of 'Rosey Carpet' U.S. Plant Pat. No. 13,965. This is a small compact plant with arching or cascading limbs.

The cultivar has been reproduced over several generations and it remains identical to the original seedling plant.

Each plant produces a number of secondary branches with inflorescences along each of the primary branches. It is not unusual to see up to 21 rather small inflorescences per primary limb including those on the secondary limbs. They, the inflorescences, range in size from 6 to 10 centimeters in length with a width of 4 to 8 centimeters.

This new cultivar reaches a height of 16 to 20 inches at maturity with substantially no vertical growth. In our growing area the plant reaches 36 to 40 inches in width. Old limbs retain their cascading form. However we have never seen any sign of defoliating bark.

Color of the tops of old growth mature limbs in Brown Group 200D, the Bottom or underside of these same limbs, are a Grey Brown 190B. The color of the tops of new growth limbs are Red Purple Group 59B. The edges of these new growth limbs carry this same 59B color along each side with a color of Yellow Green 146B on the very bottom. [Please note, these colors and all other colors used to describe all parts of this plant, in this application, are taken from The Royal Horticultural Society Colour Charts.]

Most often the leaf arrangement on Crepe Myrtle 'Cascading Pink Lady' are alternate with an occasional opposite arrangement. Leaves are ellipse or ovate with an acute tip and base. Mature leaves are relatively small in size. They vary in length of 2.7 to 3.2 centimeters and in width from 1.6 to 2.1 centimeters. Mature leaf color is a Green 137A on the Adaxial side and 137D on the abaxial, the leaf edge is also a 137D. New early growth leaves on the adaxial side are Green group 137B, the abaxial side is a Green Group 137D, edges are also a Green Group 137D with the stem or axis a Green Group 137C. Then as the leaves mature this color changes to the 137A. Bloom buds on Cascading Pink Lady are 0.5 to 0.7 cm in width and 0.7 to 1.0 cm in length. Bud color is a mostly a 145C with a few 145D with the bottom of the bud a 145B. Sepals are 0.3 cm in width and 0.9 to 1.0 cm in length. In late summer about 1 in 10 bloom buds will have a noticeable small black dot, about the size of a pin point about a 0.2 cm from the top and along the edges of where the edge of two sepals meet.

Blooms open in mid June and are in full color by June 30$^{th}$ in Zone 7B. It continues to bloom well into October. Flower color, including the edges opens with a Red Purple Group 72D, it soon fades to a 70C and then to a 70D. And occasionally the plant produces a newly opened bloom of 70C, its also not unusual to see a new bud open a 70D [both in the Red Purple Group.] This pattern of bloom change sometimes gives the appearance of a multi-colored Crepemyrtle.

This Crepemyrtle is a very cold hardy plant having survived with no damage at 8 degrees Fahrenheit. Also it is highly resistant to powdery mildew. No powdery mildew has ever been observed on the cultivar in our growing area.

It is claimed:

1. We claimed a new and a distinct variety of crepemyrtle plant substantially as described and shown, characterized by a low growing with extensive cascading lateral branching that reaches a mature height of 16 to 20 inches, with substantially no upward growth, with profuse and distinctive soft pink inflorescences that, in a consistent pattern, tend to fade as they begin to mature and this new plant has a very high resistant to powdery mildew.

* * * * *